United States Patent [19]

Walker

[11] Patent Number: 4,457,301

[45] Date of Patent: Jul. 3, 1984

[54] INTRAMEDULLARY FIXATION DEVICE

[75] Inventor: Peter S. Walker, Weston, Mass.

[73] Assignee: Howmedica Inc., New York, N.Y.

[21] Appl. No.: 389,834

[22] Filed: Jun. 18, 1982

[51] Int. Cl.³ .................. A61F 5/04; A61B 17/18
[52] U.S. Cl. .............................. 128/92 BC; 128/92 G
[58] Field of Search .......... 128/92 BC, 92 BA, 92 B, 128/92 R, 92 G

[56] References Cited

U.S. PATENT DOCUMENTS

| 2,579,968 | 12/1951 | Rush | 128/92 BC |
| 2,998,007 | 8/1961 | Herzog | 128/92 BC |
| 3,893,196 | 7/1975 | Hochman | 128/92 BC X |
| 4,011,863 | 3/1977 | Zickel | 128/92 BA |
| 4,169,470 | 10/1979 | Ender et al. | 128/92 BC |
| 4,362,163 | 12/1982 | Krick | 604/280 |

FOREIGN PATENT DOCUMENTS

| 767879 | 4/1954 | Fed. Rep. of Germany ... 128/92 BC |
| 923085 | 2/1955 | Fed. Rep. of Germany ... 128/92 BC |
| 581938 | 11/1977 | U.S.S.R. . |

Primary Examiner—Ronald L. Frinks
Attorney, Agent, or Firm—Charles J. Knuth; Peter C. Richardson

[57] ABSTRACT

An intramedullary multiple pin device for fixing fractures in the middle portion (diaphysis) of long bones. The multiple pins are resilient and held in a desired special arrangement by a flexible plastic core element.

11 Claims, 10 Drawing Figures

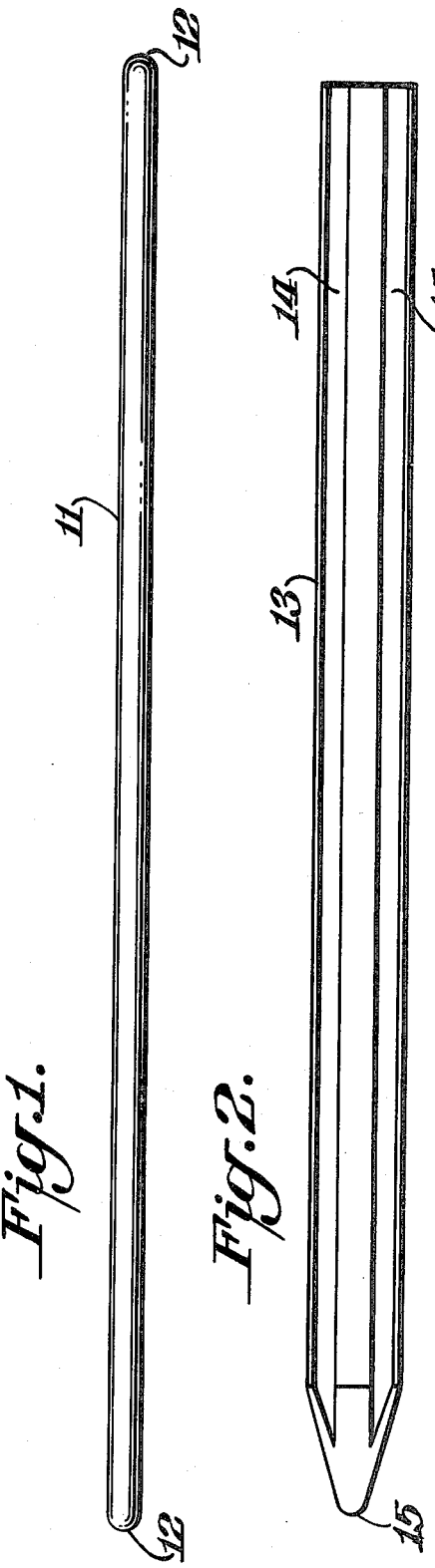
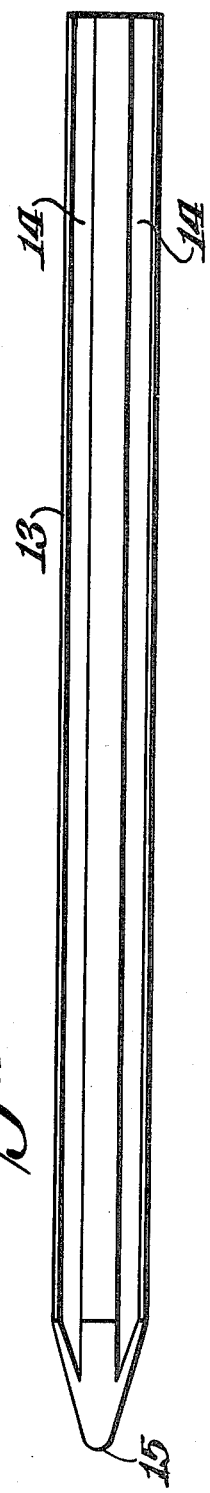
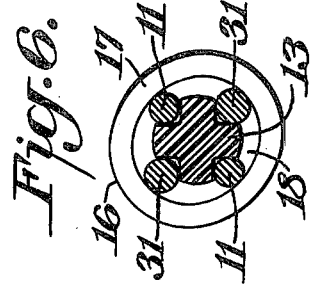
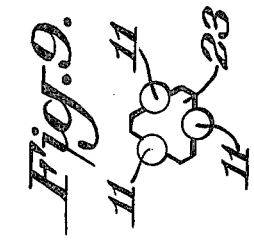
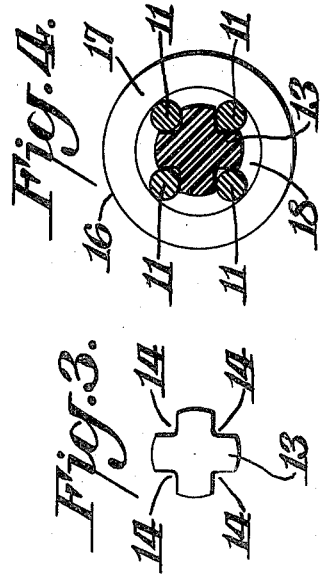

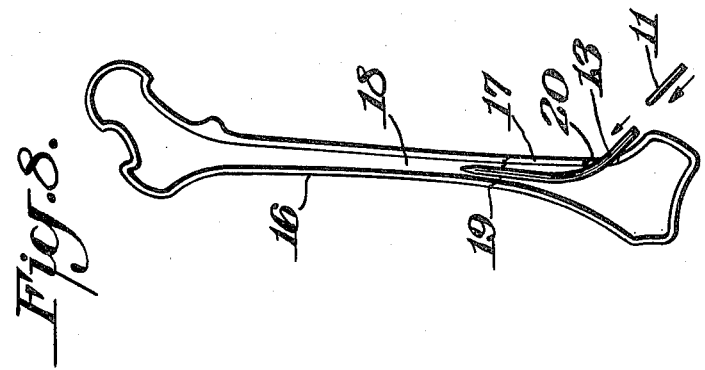
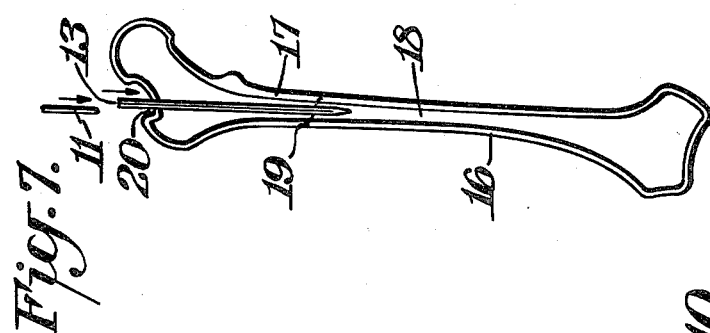
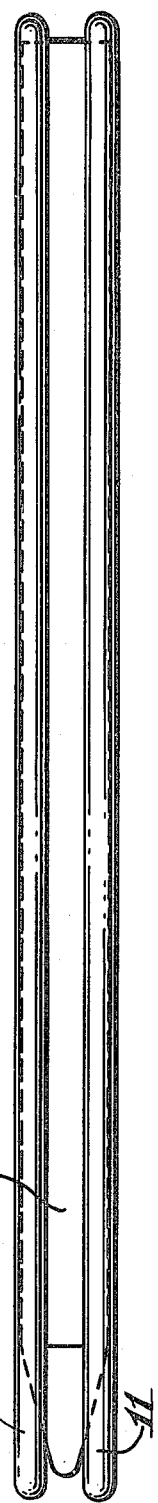

INTRAMEDULLARY FIXATION DEVICE

FIELD OF THE INVENTION

This invention relates to the fixation of fractures in long bones, especially mid bone (diaphyseal) fractures, by intramedullary support with a plurality of resilient pins.

BACKGROUND OF THE INVENTION

Intramedullary rods have been used for many years to fix fractures in the middle portion of long bones. In this technique, one or more metal rods are driven into the medullary canal of the broken bone, and through the fracture zone, leaving the rods anchored in sound bone at each end. Thus, the fracture is supported in correct position for healing. This technique has shown many benefits over alternatives such as bone plates: the patient can be mobilized and ambulated much earlier; the surgery is usually less traumatic; there is less device failure; and the bone does not suffer an excess of stress protection. Over this period, many different intramedullary rod forms have been developed, but all are basically of two types: single rods or multiple rods. Examples of single rods are those of Kuntscher, Harris (U.S. Pat. No. 4,135,507) and Halloran (U.S. Pat. No. 3,709,218). Typical multiple rod fixations are those of Ender & Ender (U.S. Pat. No. 4,169,470), Rush (U.S. Pat. No. 2,579,996), Zickel, and Herzog (U.S. Pat. No. 2,998,007).

Multiple rod use has advantages and some disadvantages over the single rod. For example, the use of a number of small diameter rods allows a precise fit in the fractured bone, but they may not impart sufficient stability for some fractures.

SUMMARY OF THE INVENTION

The intramedullary bone fracture fixation device of this invention comprises several resilient small diameter rods (pins) held apart over substantially their whole length and in a desired arrangement by a flexible core element. The length of the pin-core combination will vary according to the application. It is selected to be long enough to extend longitudinally through the fracture zone and into the medullary canal of sound bone on both sides. It should extend an appreciable distance beyond the fracture zone on both sides to stabilize the fracture. The pins and core element may be made in different cross sectional sizes so that their assembled cross sections can accurately fit in medullary canals of different diameters, and non-circular cross-sections.

Preferably, there are longitudinal grooves in the core sides into which the pins are placed and held against compact bones at the periphery of the medullary canal. The grooves are less than one pin diameter deep so that pin sides will project out as longitudinal ridges into cancellous bone in the intramedullary space and against the endosteal cortex. These ridges provide rotational stability through their resistance to torsion. Additional resistance to rotation can be achieved by having the distal ends of the pins extend beyond the core into undisturbed cancellous bone.

This new intramedullary fixation device provides a combination of advantages not found in previous devices. The components have simple forms and thus are of relatively low cost. With only a few different diameter pins and cores, a combined cross section can be created to closely fit a wide range of medullary canal diameters. This good fit ensures firm anchorage of the pins against the compact bone. Little or no reaming is required for its implacement and space is preserved between the device and the compact bone to maintain vascularity.

It is an important aspect of this invention that the core be flexible relative to the pins to maintain, in the assembled device, the resilience of the pins. It has been found desirable for rapid and strong healing that a fracture not be over protected from physiological stress. Therefore, a fracture fixation device should permit transfer of some stress to the fracture zone by deforming slightly under load, but it should be resilient to spring back into correct position when the stress is removed. The device of this invention also provides for beneficial axial impaction of the fracture, because the device has low resistance to axial movement (low axial stiffness).

DESCRIPTION OF THE DRAWINGS

FIG. 1 is a side view of a pin useful in this invention.
FIG. 2 is a side view of a core element of this invention, designed to hold four pins.
FIG. 3 is an end view of the FIG. 2 core.
FIG. 4 is a cross section view of an assembled four-pin device as placed in a long bone as shown in FIG. 6.
FIG. 5 is an end view of a centrally cannulated core.
FIG. 6 is the same view as in FIG. 4, but showing use of different diameter pins to fit a noncircular medullary canal.
FIG. 7 is an illustration of the method of implanting the device through the trochaneric end of the femur.
FIG. 8 is an illustration of the method of implanting the device through the condylar end of the femur.
FIG. 9 is an end view of an assembled three-pin device employing a triangular core.
FIG. 10 is a side view of an assembled four-pin device showing pins slightly longer than the core.

DESCRIPTION OF PREFERRED EMBODIMENTS

The intramedullary bone fracture fixation device of this invention is a combination of resilient, long pins and a flexible core which holds the pins apart in a desired arrangement. The preferred embodiments uses metal pins, equally spaced from each other by a plastic core.

The pins are the chief stress bearing members and must be stiff without being rigid. They must be resilient to return to their original position when bent. They are preferably made in the form of long thin rods of circular cross section and from a body compatible resilient metal. The desired combination of stiffness, resilience and corrosion resistance is satisfactorily achieved by pins made from titanium alloys, preferably Ti-6Al-4V. However, other materials can be used, such as stainless steels, cobalt-chromium alloys and fiber reinforced composites. FIG. 1 shows a side view of a preferred form of pin. The pin 11 has rounded ends 12. A typical pin is 2.7 millimeters in diameter and 165. millimeters in length, but useful pins can range from about 2-4.5 millimeters in diameter and about 75-250 millimeters in length depending on the size and length of the fractured bone.

The preferred form for a core is shown in FIGS. 2 and 3. This core 13 is of generally circular cross section, but with four longitudinal grooves 14 equally spaced around its periphery. These grooves serve to guide the pins into place on insertion and to hold them in an approximately parallel position to support the fracture during healing. The longitudinal core grooves can have various cross-section forms, but must give lateral support to the pins and have a depth of less than one pin diameter. This shallow depth ensures that the sides of the pins will project radially out from the core surface as longitudinal ridges. To aid insertion of the core into the medullary canal of a bone, the distal end of the core is tapered to a blunt point 15. A typical core is 8.3 mm. in diameter with four longitudinal grooves each about 3 mm. wide and about 1.4 mm. deep. However, cores will range from about 5–12 mm. diameter and about 70–230 mm. in length. FIG. 10 shows a side view of the FIGS. 2 and 3 type core holding four pins, as the device might be assembled in the medullary canal of a long bone. In this preferred form of the device, the pins are slightly longer than the core. Only two pins can be seen in this side view.

While the presently preferred core has a generally circular cross-section and is particularly useful for fixing fractures of the femur, different cross-sections such as triangular or square, might be advantageous for use in special situations. A square core might have a cross-section very similar to that of FIG. 3. A triangular core might be chosen for fixing the tibia and other bones having approximately triangular cross-section medullary canals. Such a core would support three pins and could have the generally triangular form 23 shown as an end view in FIG. 9. In any case, the core must be flexible. This aids in its insertion into the bone as shown in FIG. 8 and, when in place, prevents the pin-core combination from being so rigid that the combination acts like a solid rod fixation device. Ultra-high molecular weight polyethylene is the preferred core material, in part because of its good lubricant quality with metal pins, but other materials can be used, such as polypropylene, polysulfone, polyacetal or fiber reinforced composites.

A device according to this invention is especially useful for fixing fractures of the femur shaft. FIG. 7 illustrates a trochanteric insertion of this device to stabilize a fracture near the proximal end of the shaft of femur 16. A hole 20 is opened in the intercondylar notch beside the greater trochanter, giving access to the medullary canal 18. The canal may be probed across the fracture zone 19 to make insertion of the core 13 easier. Infrequently, it may be desirable to ream the canal before inserting the core. With the fracture properly aligned, the core is inserted through hole 20 and driven into the medullary canal 18 until it extends beyond the fracture zone 19. Pins 11 are then driven in to be essentially co-extensive with the core, guided into place by the core grooves. Normally, the driven ends of the pins and core are not forced all the way into the bone. Enough of each is left exposed so that their ends can be gripped when removal is indicated.

As can be seen from FIGS. 4 and 10, the pins are held firmly in their peripheral positions over essentially their entire length between core 13 and compact bone 17. It is preferable to select pins slightly longer than the core, and drive them into undisturbed cancellous bone beyond the distal end of the core. This provides increased rotational stability.

Pins and cores are made in a range of diameters. For a given use, pin and core diameters are selected so that the sides of the pins in the assembled device will fit firmly against the compact layer 17 of bone 16. Pins of different diameters will frequently be required in a given application to custom fit the assembled device into the patient's fractured bone. FIG. 6 shows how an elliptical medullary canal can be fitted by use of two small diameter pins 11 oppositely placed to two larger diameter pins 31. Unlike other multiple pin fixations, there can be no contact between the metal pins to chafe and produce metal debris.

FIG. 8 illustrates a condylar insertion into a femur to stabilize a fracture near the distal end of the shaft. In this case, a hole 20 is made into the side of the femur above a distal condyle. Insertion of the device follows the same procedure as described in connection with FIG. 7, except that the inherent flexibility of the core and pins is brought into play during insertion through the laterally placed hole as shown.

More accurate placement of a core is possible if a guide pin is first driven through the reduced fracture zone and if a cannulated core is is used. In this case, the core is inserted over the guide pin with less chance of disturbing the fracture. One form of cannulated core is shown as an end view in FIG. 5. A longitudinal bore 22 extends completely through cannulated core 13 so that the core can be driven into place over a guide pin. The guide pin is later removed.

While the utility of this device has been illustrated for fixing diaphyseal fractures of the femur, it is not limited to that use. Similar fractures of other long bones, such as the tibia and the humerus, are equally fixable. Essentially, only selection of appropriate pin and core diameters and lengths will be different.

A major advantage of this invention is increased stability of the fracture during healing. The stress bearing pins are held at the periphery of the medullary canal, where they can best resist torsional and flexural loads. A further advantage is that the core causes the pins to cooperate in equally resisting flexural stress from all angles. Previous multiple pin fixations, for example, those of Rush or Enders, do not offer this same stability.

Another advantage of this invention is that the pin sides extend out from the core surface leaving vascular tissue between core and compact bone to allow continued near normal vascularity.

The core holds the pins in a desired pattern over essentially their entire length. Without a core, the intramedullary tissue being relatively soft, multiple thin pins or rods cannot be prevented from shifting position under transverse, torsional and flexural stresses. Such shifting results in a less stable fixation and can result in malunion of the fracture. Thus, the core is an important feature of this invention. However, the core must be flexible relative to the pins, and not interfere with the beneficial slight springiness the pins impart to the assembled device. A relatively inflexible core would result in an assembly that would function very little different from a single large diameter rod. A single large diameter rod fixation can provide rigidity, but, in the context of fracture fixation, rigidity is not synonymous with stability. Stability implies sufficient control of transverse, torsion and flexural stress to prevent displacement of fracture ends, but not such complete control as to eliminate those stresses below a level beneficial to healing.

The fixation device of this invention has relatively low resistance to axial movement in the bone. Therefore, it allows some axial impaction of the fracture, which also aids the healing process.

This invention has been described in the form of the presently preferred embodiment. A few alternate design features have been suggested. However, it can be appreciated that many changes in design can be made without departing from the spirit of the invention. For example, different numbers of pins might be used; the pins could be of non-circular cross-sections; the cores could be slightly tapered to hold pins in a non-parallel configuration; the distal end shapes of pins and cores could be differently formed. Consequently, the invention is to be limited only by the scope of the appended claims.

I claim:

1. An intramedullary bone fracture fixation device comprising, a plurality of thin resilient pins substantially longer than the fracture zone to be fixed and a flexible core element holding the pins apart from one another in a desired spacial arrangement over substantially the full length of the pins, with said pins being held in sliding fit in longitudinal grooves in the periphery of said flexible core.

2. The intramedullary fixation device of claim 1 wherein the pins are metal and the core is plastic.

3. The intramedullary fixation device of claim 1 or 2 wherein the pins are of circular cross section with rounded distal ends, held in longitudinal grooves equally spaced around the core periphery and of depth less than one pin diameter, the core having a blunt pointed distal end.

4. The intramedullary fixation device of claim 3 wherein said pins are longer than said core.

5. The intramedullary fixation device of claim 3 wherein there is an axial bore through the core.

6. The intramedullary fixation device of claim 3 wherein four pins are used.

7. The intramedullary fixation device of claim 3 wherein three pins are used and the core has a generally triangular cross-section.

8. An intramedullary bone fracture fixation device comprising the combination of four resilient metallic pins of 2–4.5 millimeter diameter, 75–250 millimeter length with rounded distal ends, held apart in longitudinal grooves in the surface of a flexible plastic core of 5–12 millimeter diameter, 70–230 millimeter length, the longitudinal grooves being less than one pin diameter deep and equally spaced around the periphery of the core, the core being slightly shorter than the pins and tapering to a blunt point at the distal end.

9. The intramedullary fixation device of claim 8 wherein the pins are made of titanium alloy Ti-6Al-4V, and the core is made of ultra-high molecular weight polyethylene.

10. A method of stabilizing a fracture of a long bone of a patient comprising the steps of:
    (a) inserting a flexible elongated core element provided with a plurality of longitudinal grooves in the periphery thereof into the medullary canal of the fractured bone until said core extends through the fracture zone; and
    (b) then inserting a thin resilient pin into each of said longitudinal grooves so that said pins are held apart in compression between the patient's bone structure and said core in a desired spacial arrangement over substantially the entire lengths of said pins,
    with said pins and said core being positioned at the completion of said step (b) to extend through the fracture zone and into the medullary canal of sound bone on both sides of the fracture.

11. A method of claim 10 wherein said flexible core element is made of plastic, said resilient pins are made of metal, said core element has a blunt pointed distal end, said pins are of circular cross-section with rounded distal ends, and said longitudinal grooves are equally spaced around the periphery of said core element and are each of a depth less than one diameter of the pin received thereby.

* * * * *